United States Patent
Fortier et al.

(10) Patent No.: US 8,876,021 B2
(45) Date of Patent: *Nov. 4, 2014

(54) SILICONE SPRAY TIP

(71) Applicant: Confluent Surgical, Inc., Bedford, MA (US)

(72) Inventors: Jason Fortier, Concord, MA (US); Les Hull, Attleboro, MA (US); Art Driscoll, Reading, MA (US)

(73) Assignee: Confluent Surgical, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/758,198

(22) Filed: Feb. 4, 2013

(65) Prior Publication Data

US 2013/0146679 A1    Jun. 13, 2013

Related U.S. Application Data

(63) Continuation of application No. 13/247,408, filed on Sep. 28, 2011, now Pat. No. 8,387,899, which is a continuation of application No. 12/427,965, filed on Apr. 22, 2009, now Pat. No. 8,033,483.

(60) Provisional application No. 61/047,826, filed on Apr. 25, 2008.

(51) Int. Cl.
*B05B 7/10* (2006.01)
*B01F 5/06* (2006.01)
(Continued)

(52) U.S. Cl.
CPC .............. *B05B 7/0408* (2013.01); *B01F 5/0656*
(Continued)

(58) Field of Classification Search
USPC ......... 239/106, 107, 399, 432, 437, 418, 427, 239/433, 434, 303–305, 490–494, 533.13, 239/533.14, 588, 597, 602, DIG. 12; 222/137, 145.1, 145.5, 145.6, 327; 604/82, 83, 187, 191, 240
See application file for complete search history.

(56) References Cited

U.S. PATENT DOCUMENTS 3,214,102 A    10/1965  Meyer
3,828,980 A     8/1974  Creighton et al.
(Continued)

FOREIGN PATENT DOCUMENTS

EP    1 955 660    8/2008
EP    2 111 918   10/2009

OTHER PUBLICATIONS

European Search Report EP 10 25 1809 dated Jul. 5, 2013.

*Primary Examiner* — Steven J Ganey
(74) *Attorney, Agent, or Firm* — Carter, DeLuca, Farrell & Schmidt, LLP

(57) ABSTRACT

An applicator assembly for mixing at least a first and second component is provided. The applicator assembly includes a manifold configured for operable engagement with at least a first and second source of component, the manifold including at least a first and second component channel therethrough, an elongated shaft extending distally from the manifold, the elongated shaft including at least a first and second component lumen extending the length thereof, the at least first and second component channels in fluid communication with the at least first and second component channels, a tip assembly defining a first chamber, an intermediate chamber and a final chamber.

17 Claims, 8 Drawing Sheets

(51) Int. Cl.
*A61B 17/00* (2006.01)
*B05B 7/04* (2006.01)
*B01F 5/00* (2006.01)
*B01F 13/00* (2006.01)
*B05B 1/34* (2006.01)
*B05B 15/06* (2006.01)
*B01F 15/00* (2006.01)
*B05B 15/02* (2006.01)

(52) U.S. Cl.
CPC (2013.01); *B01F 2005/0637* (2013.01); *A61B 17/00491* (2013.01); *B05B 7/10* (2013.01); *A61B 2017/00495* (2013.01); *B01F 5/0057* (2013.01); *B01F 13/0027* (2013.01); *Y10S 239/12* (2013.01); *B05B 1/3436* (2013.01); *B05B 15/066* (2013.01); *B01F 15/0087* (2013.01); *B05B 15/0291* (2013.01)
USPC ........... 239/399; 239/432; 239/433; 239/490; 239/491; 239/493; 239/533.13; 239/588; 239/602; 239/DIG. 12; 239/303; 222/137; 222/145.1; 604/82; 604/191

(56) References Cited

U.S. PATENT DOCUMENTS

| | | | |
|---|---|---|---|
| 4,040,420 | A | 8/1977 | Speer |
| 4,359,049 | A | 11/1982 | Redl et al. |
| 4,538,920 | A | 9/1985 | Drake |
| 4,631,055 | A | 12/1986 | Redl et al. |
| 4,735,616 | A | 4/1988 | Eibl et al. |
| 4,753,536 | A | 6/1988 | Spehar et al. |
| 4,767,026 | A | 8/1988 | Keller et al. |
| 4,767,416 | A | 8/1988 | Wolf et al. |
| 4,842,581 | A | 6/1989 | Davis |
| 4,874,368 | A | 10/1989 | Miller et al. |
| 4,978,336 | A | 12/1990 | Capozzi et al. |
| 4,979,942 | A | 12/1990 | Wolf et al. |
| 5,033,650 | A * | 7/1991 | Colin et al. ............... 222/145.6 |
| 5,049,135 | A | 9/1991 | Davis |
| 5,104,375 | A | 4/1992 | Wolf et al. |
| 5,116,315 | A | 5/1992 | Capozzi et al. |
| 5,249,709 | A | 10/1993 | Duckworth et al. |
| 5,249,862 | A | 10/1993 | Herold et al. |
| 5,328,462 | A | 7/1994 | Fischer |
| 5,333,760 | A | 8/1994 | Simmen |
| 5,413,253 | A | 5/1995 | Simmen |
| 5,445,614 | A | 8/1995 | Haber et al. |
| 5,474,540 | A | 12/1995 | Miller et al. |
| 5,605,255 | A | 2/1997 | Reidel et al. |
| 5,643,206 | A | 7/1997 | Fischer |
| 5,665,066 | A | 9/1997 | Fischer |
| 5,740,965 | A | 4/1998 | Miyagi et al. |
| 5,810,885 | A | 9/1998 | Zinger |
| 5,819,988 | A | 10/1998 | Sawhney et al. |
| 5,890,655 | A | 4/1999 | Collias et al. |
| RE36,235 | E | 6/1999 | Keller et al. |
| 5,941,462 | A | 8/1999 | Sandor |
| 6,047,861 | A | 4/2000 | Vidal et al. |
| 6,065,645 | A | 5/2000 | Sawhney et al. |
| 6,132,396 | A | 10/2000 | Antanavich et al. |
| 6,161,730 | A | 12/2000 | Heusser et al. |
| 6,328,229 | B1 | 12/2001 | Duronio et al. |
| 6,398,761 | B1 | 6/2002 | Bills et al. |
| 6,527,749 | B1 | 3/2003 | Roby et al. |
| 6,585,696 | B2 | 7/2003 | Petersen et al. |
| 6,609,666 | B1 | 8/2003 | Blake |
| 6,648,852 | B2 | 11/2003 | Wirt et al. |
| 6,698,622 | B2 | 3/2004 | Sawhney et al. |
| 6,752,292 | B2 | 6/2004 | Van Herpen |
| 6,769,574 | B1 | 8/2004 | Keller |
| 6,773,414 | B2 | 8/2004 | Ljungquist |
| 6,783,514 | B2 | 8/2004 | Tovey et al. |
| 6,820,766 | B2 | 11/2004 | Keller et al. |
| 6,835,186 | B1 | 12/2004 | Pennington et al. |
| 6,852,099 | B2 | 2/2005 | Redl et al. |
| 6,884,232 | B1 | 4/2005 | Hagmann et al. |
| 6,921,381 | B2 | 7/2005 | Spero et al. |
| 6,994,686 | B2 | 2/2006 | Cruise et al. |
| 7,124,574 | B2 | 10/2006 | Horn et al. |
| 7,124,914 | B2 | 10/2006 | Foster et al. |
| 7,128,278 | B2 | 10/2006 | Archambeau et al. |
| 7,131,597 | B2 | 11/2006 | Scattergood |
| 7,140,558 | B2 | 11/2006 | McCracken et al. |
| 7,140,560 | B2 | 11/2006 | Stotts et al. |
| 7,140,797 | B2 | 11/2006 | Hunter et al. |
| 7,152,396 | B2 | 12/2006 | Cheng |
| 7,152,813 | B2 | 12/2006 | Chen |
| 7,156,835 | B2 | 1/2007 | Epstein |
| 7,159,796 | B2 | 1/2007 | Yquel |
| 7,164,133 | B2 | 1/2007 | Hjertman et al. |
| 7,172,733 | B2 | 2/2007 | Gauthier et al. |
| 7,178,742 | B2 | 2/2007 | Mellentine et al. |
| 7,178,743 | B2 | 2/2007 | Clarke, III et al. |
| 7,178,744 | B2 | 2/2007 | Tapphorn et al. |
| 7,182,279 | B2 | 2/2007 | Wang |
| 7,185,829 | B2 | 3/2007 | Sundholm |
| 7,191,917 | B2 | 3/2007 | Brinz et al. |
| 7,191,959 | B2 | 3/2007 | Kutay et al. |
| 7,195,135 | B1 | 3/2007 | Garcia et al. |
| 7,195,180 | B2 | 3/2007 | Lee |
| 7,201,336 | B2 | 4/2007 | Blette et al. |
| 7,207,969 | B2 | 4/2007 | Epstein et al. |
| 7,217,254 | B2 | 5/2007 | Kirwan et al. |
| 7,222,752 | B2 | 5/2007 | Ponton |
| 7,223,426 | B2 | 5/2007 | Cheng et al. |
| 7,225,999 | B2 | 6/2007 | Foianini et al. |
| 7,232,080 | B2 | 6/2007 | Kutay et al. |
| 7,232,082 | B2 | 6/2007 | Muhlhausen et al. |
| 7,237,693 | B2 | 7/2007 | Brennan et al. |
| 7,237,726 | B2 | 7/2007 | Yu |
| 7,244,248 | B2 | 7/2007 | Azzolini |
| 7,246,758 | B2 | 7/2007 | Wang |
| 7,252,243 | B2 | 8/2007 | Bjorn et al. |
| 7,252,247 | B2 | 8/2007 | Holm et al. |
| 7,264,179 | B2 | 9/2007 | Robbins |
| 7,267,288 | B2 | 9/2007 | Wheeler, Jr. et al. |
| 7,270,654 | B2 | 9/2007 | Griego et al. |
| 7,275,699 | B2 | 10/2007 | Schmidt |
| 7,278,985 | B2 | 10/2007 | Agerup |
| 7,611,494 | B2 | 11/2009 | Campbell et al. |
| 7,811,291 | B2 | 10/2010 | Liu et al. |
| 7,833,216 | B2 | 11/2010 | Voegele et al. |
| 8,033,483 | B2 * | 10/2011 | Fortier et al. ............... 239/433 |
| 8,387,899 | B2 * | 3/2013 | Fortier et al. ............... 239/399 |
| 2002/0104851 | A1 | 8/2002 | Parise |
| 2002/0156435 | A1 | 10/2002 | Emmons |
| 2002/0165483 | A1 | 11/2002 | Miller et al. |
| 2003/0062426 | A1 | 4/2003 | Gregory et al. |
| 2003/0183653 | A1 | 10/2003 | Bills |
| 2003/0209612 | A1 | 11/2003 | Hahnen |

* cited by examiner

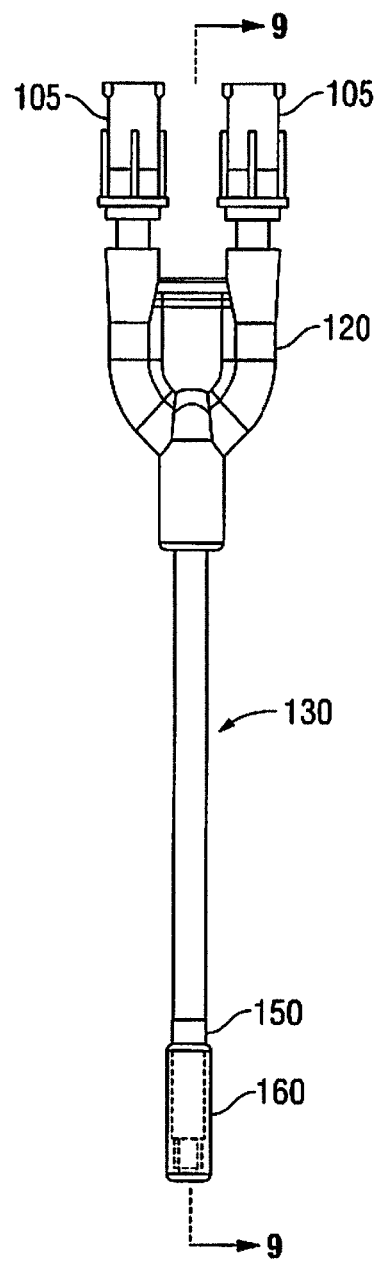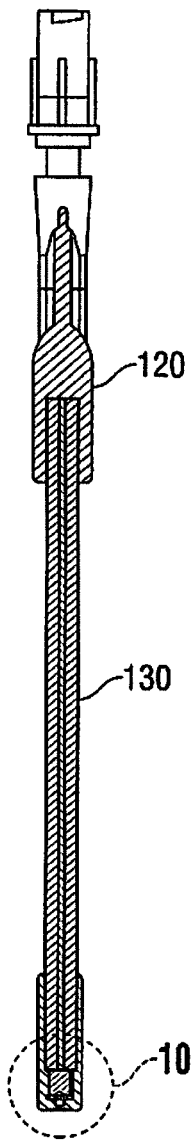
FIG. 8  FIG. 9

SILICONE SPRAY TIP

CROSS-REFERENCE TO RELATED APPLICATION

This application is a continuation of U.S. application Ser. No. 13/247,408 filed Sep. 28, 2011, now U.S. Pat. No. 8,387,899, which is a continuation of U.S. application Ser. No. 12/427,965 filed Apr. 22, 2009, now U.S. Pat. No. 8,033,483, which claims benefit of application Ser. No. 61/047,826 filed Apr. 25, 2008, and the disclosures of each of the above-identified applications are hereby incorporated by reference in their entirety.

BACKGROUND

1. Technical Field

The present disclosure relates to assemblies for mixing and applying two or more components. More particularly, the present disclosure relates to a spray tip for use with an applicator assembly for mixing two or more components.

2. Background of Related Art

Applicator assemblies for dispensing two or more components are known. In the field of medical devices, such assemblies are used for applying bioadhesives, polymers and other synthetic material used in wound closure. Because of the reactant nature of the components used to form the bioadhesive, mixing of the components does not occur until the solution is ready to be applied. Mixing of the components too soon before application may result in premature hardening of the mixture, thereby making application of the solution impossible. Thus, in known applicator assemblies, the two or more components are maintained separately until just prior to application. The applicator assemblies include one or more mixing means for mixing the two or more solutions prior to application. The mixing means may be passive, e.g. spiral configuration in the tubing, or instead may be active, e.g. mixing blade or impeller. Once mixed, the solution may be applied through a needle-like output or may instead be ejected through a spray assembly. Thorough mixing of the two or more components prior to application is important to ensure the solution will perform as intended.

SUMMARY

Accordingly, an applicator assembly for mixing at least a first and second component is provided. The applicator assembly includes a manifold configured for operable engagement with at least a first and second source of component, the manifold including at least a first and second component channel therethrough, an elongated shaft extending distally from the manifold, the elongated shaft including at least a first and second component lumen extending the length thereof, the at least first and second component channels in fluid communication with the at least first and second component channels, a tip assembly defining a first chamber, an intermediate chamber and a final chamber, wherein the first chamber is configured to receive a distal end of the elongated shaft, the second chamber is configured to receive an insert, and the final chamber is configured to receive the at least partially mixed at least first and second components prior to the mixture being ejected from an outlet defined in the distal end of the tip assembly.

The elongated shaft may include a flexible wire extending the length thereof. The manifold and elongated member may be integrally formed. The intermediate chamber may include ribs for maintaining the insert in a space relationship from a wall of the chamber. The outlet may be configured to eject the mixture from the tip assembly as a spray. The applicator assembly may further include at least a first slot formed between the intermediate chamber and the final chamber configured to direct the at least first and second components radially inward. In one embodiment, the tip assembly includes three or more slots. The at least first slot may be configured to cause the swirling of the at least first and second components within the final chamber. The insert may include a substantially cylindrical body configured to be received within the intermediate chamber. The manifold may include a substantially Y-shaped member. The elongated shaft and/or the insert may be composed of silicone. The elongated shaft may be flexible.

Also provided is a system for mixing at least a first and second component. The system includes at least a first and second source of component, a manifold configured for operable engagement with the at least first and second source of component, the manifold including at least a first and second component channel therethrough, an elongated shaft extending distally from the manifold, the elongated shaft including at least a first and second component lumen extending the length thereof, the at least first and second component channels in fluid communication with the at least first and second component channels, a tip assembly defining a first chamber, an intermediate chamber and a final chamber, wherein the first chamber is configured to receive a distal end of the elongated shaft, the second chamber is configured to receive an insert, and the final chamber is configured to receive the at least partially mixed at least first and second components prior to the mixture being ejected from an outlet defined in the distal end of the tip assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 8 is a top plan view of the applicator assembly of FIG. 7;

FIG. 9 is a cross-sectional side view of the applicator assembly of FIGS. 7 and 8, taken along line 9-9 of FIG. 8.

DETAILED DESCRIPTION

Figure 1:
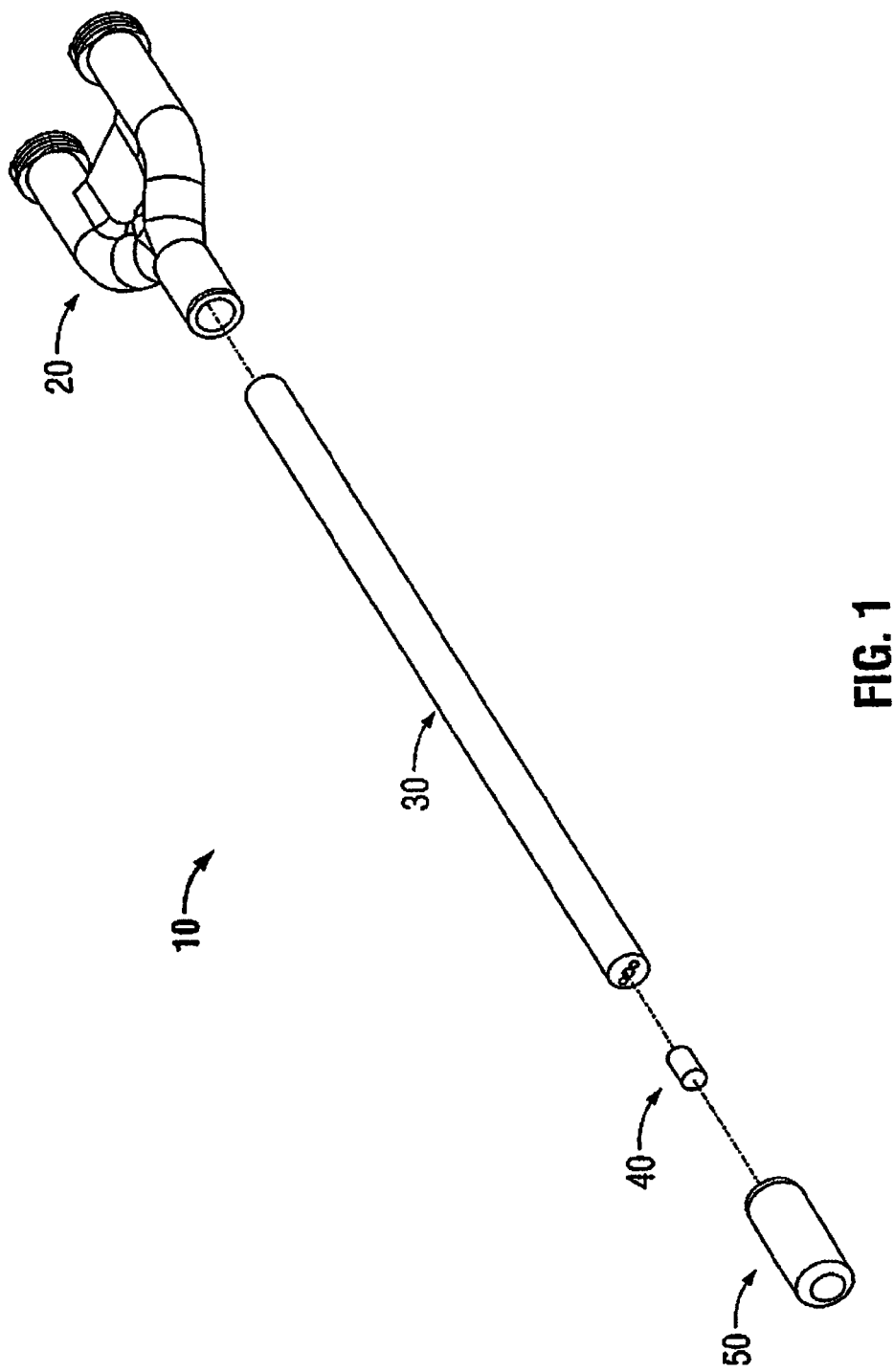
FIG. 1 is an exploded perspective view of an applicator assembly including a spray tip assembly according to an embodiment of the present disclosure.

Referring initially to FIG. 1, an applicator assembly including a spray tip assembly according the present disclosure is shown generally as applicator assembly 10. Applicator assembly 10 includes a manifold or base 20, an elongated shaft 30 extending from manifold 20, and a spray tip assembly 50 positioned on a distal end 30b of elongated shaft 30. Applicator assembly 10 further includes an insert 40 configured to be received within spray tip assembly 50 and distal of elongated shaft 30.

Figure 2:
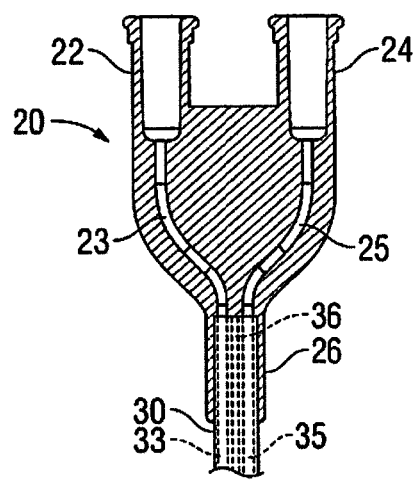
FIG. 2 is a cross-sectional side view of a manifold of the applicator assembly of FIG. 1.

With reference now to FIG. 2, manifold 20 includes a substantially Y-shaped member having first and second proximal extension 22, 24 and a distal extension 26. Proximal extensions 22, 24 are configured for operable engagement with a first and second source of component (not show), e.g. syringe. Distal extension 26 is configured for operable engagement with elongated shaft 30, as will be discussed in further detail below. Manifold 20 further includes first and second component channels 23, 25. First and second component channels 23, 25 fluidly communicate the first and second sources of component with a first and second lumen 33, 35 formed in elongated shaft 30. While manifold 20, as shown, is configured to receive only two sources of component, it is envisioned that manifold 20 may be configured to receive more than two sources of component.

Referring back to FIG. 1, elongated shaft 30 defines a substantially solid body of silicone, plastic, polymer or other flexible material. As noted above, elongated shaft 30 includes first and second component lumen 33, 35 extending the length thereof. A wire 36 composed of a malleable material also extends the length of elongated shaft 30. Wire 36 is configured to maintain elongated shaft 30 in a bent or flexed configuration after elongated shaft 30 has been bent or flexed to accommodate a given procedure. Elongated shaft 30 is secured to distal extension 26 of manifold 20 such that first and second component lumen 33, 35 align with first and second component channels 23, 25, respectively. Alternatively, elongated shaft 30 may be integrally formed with manifold 20. Elongated shaft 30 may further include grooves, detents or otherwise be configured for secure engagement with spray tip assembly 50.

Figure 3:
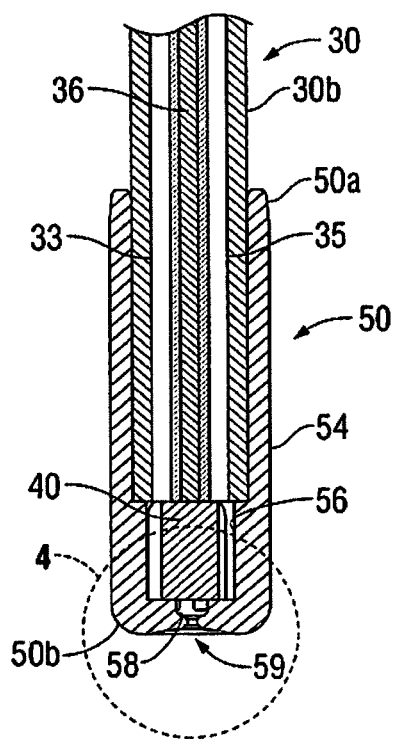
FIG. 3 is a cross-sectional side view of the spray tip assembly of the applicator assembly of FIG. 1.

With reference now to FIGS. 3-6, spray tip assembly 50 defines a substantially cylindrical body 52 having an open proximal end 52a and a substantially closed distal end 52b. Open proximal end 52a is configured to receive distal end 30b of elongated shaft 30 (FIG. 3). As will be discussed in further detail below, distal end 52b includes an outlet 59 configured to eject a thoroughly mixed solution. Spray tip assembly 50 may be composed of silicone or other suitable biocompatible materials.

In one embodiment, spray tip assembly 50 is composed of a silicone elastomer, for example, TUFEL® II 94706, a silicone rubber compound or LIM®6071, a liquid silicone rubber, available from Momentive Performance Materials, Waterford, N.Y. Through testing, it has been found that a spray tip assembly 50 composed of silicone having a 70 durometer, spray tip assembly 50 is capable of unclogging itself during operation. The flexible nature of silicone permits spray tip assembly 50 to flex under the increased pressure experienced during a clog of spray tip assembly 50. The flexion of spray tip assembly 50 dislodges any clog that may form therein. Additionally, the non-wetting surface characteristic (hydrophobicity) of silicone may assist in preventing the clogging of spray tip assembly 50. The ability of spray tip assembly 50 to unclog itself during operations permits the continuous use of applicator assembly 10 without the need to repeatedly change spray tip assembly 50. In this manner, the length of the procedure may be reduced and the expense of using multiple spray tip assemblies is eliminated.

Figure 3A:
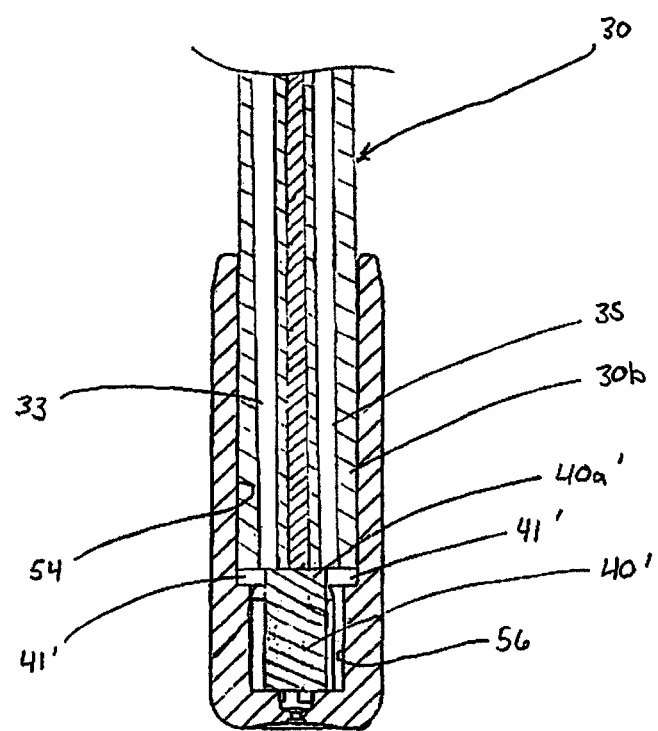
FIG. 3A is a cross-sectional side view of an alternative embodiment of the insert of the applicator assembly of FIG. 3.
Figure 4:
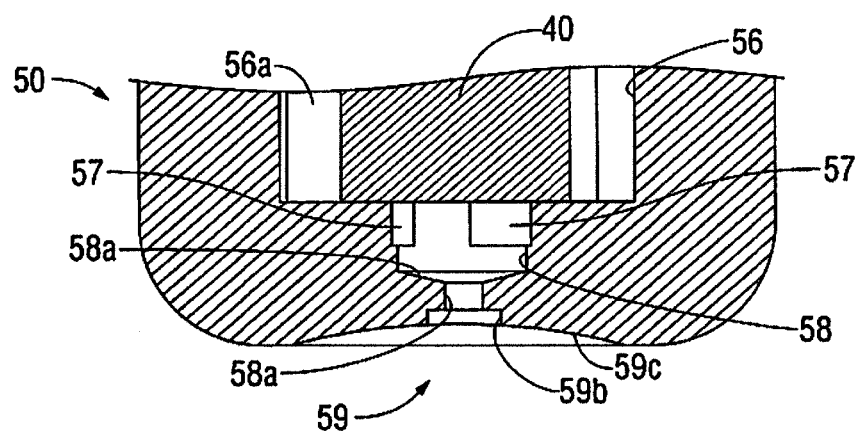
FIG. 4 is an enlarged cross-sectional view of the distal end of the spray tip assembly of FIG. 3.
Figure 5:
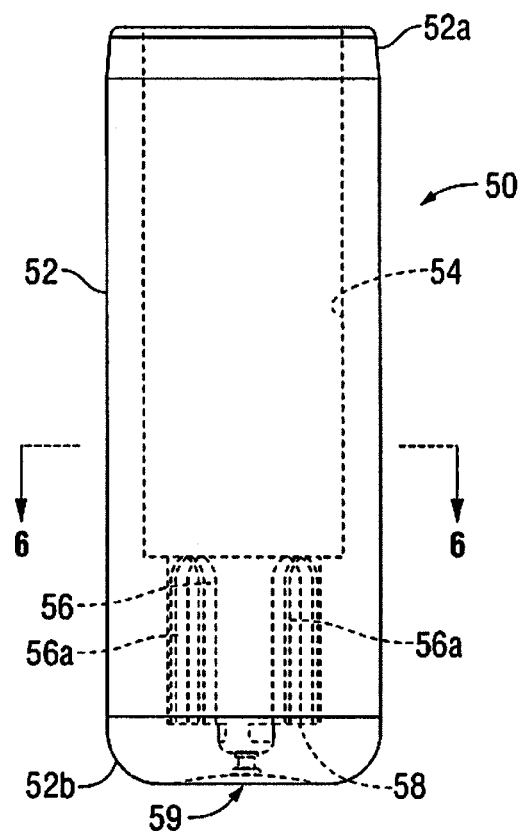
FIG. 5 is a side view of the spray tip assembly of FIGS. 3 and 4.

Still referring to FIGS. 3-6, spray tip assembly 50 includes a first chamber 54, an intermediate chamber 56 and a final chamber 58. First chamber 54 defines a substantially cylindrical cavity for receiving distal end 30b of elongated shaft 30. As will be discussed in further detail below, first chamber 54 is configured such that distal end 30b of elongated shaft 30 is received pressed flush against insert 40. It is envisioned, however, that first chamber 54 may be configured such that distal end 30b of elongated shaft 30 is proximally spaced from insert 40 so as to form an initial mixing space for the first and second components. Intermediate chamber 56 defines a substantially cylindrical cavity configured to receive insert 40. Intermediate chamber 56 includes ribs or spacers 56a for maintaining insert 40 (shown in phantom in FIG. 6) centered within intermediate chamber 56. Insert 40 includes a solid, substantially cylindrical member positioned within intermediate chamber 56 to force the first and second components to flow around insert 40 in the space recreated by ribs 56a. In an alternative embodiment (FIG. 3A), insert 40' may extend proximally from intermediate chamber 56 into first chamber 54, thereby creating an initial mixing space 41' between distal end 30b of elongated shaft 30 and intermediate chamber 56 about a proximal end 40a' of insert 40'. In this manner, the first and second components flowing from first and second component lumen 33, 35 may initially mix prior to entering intermediate chamber 56. Inserts 40, 40' may be composed of silicone or other suitable biocompatible material.

Figure 6:
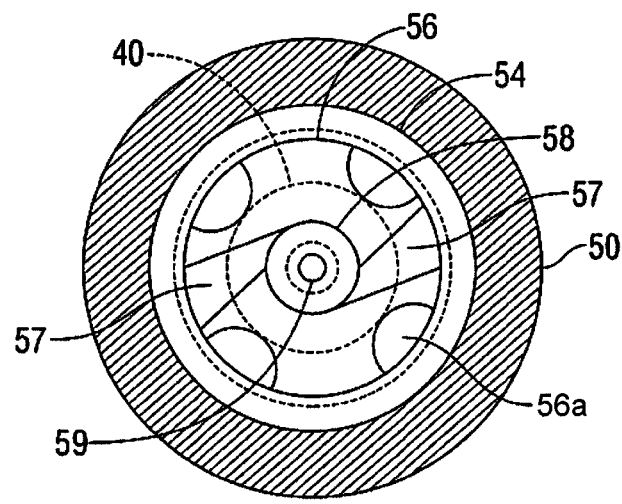
FIG. 6 is a cross-sectional view of the spray tip assembly of FIG. 5 taken along line 6-6.
Figure 6A:
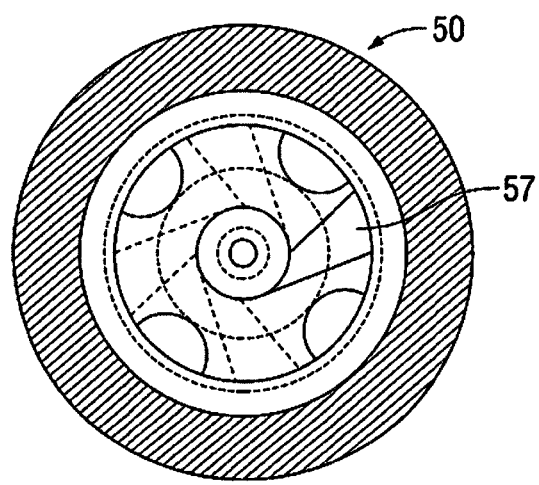
FIG. 6A is a cross-sectional view of an alternate embodiment of the spray tip of FIG. 6.

With reference still to FIGS. 3-6, final chamber 58 defines a substantially cylindrical cavity having a tapered distal portion 58a. Spray tip assembly 50 includes slots 57 formed therein fluidly communicating intermediate chamber 56 and final chamber 58. Slots 57 define opposed openings angling outwardly from final chamber 58 between a line tangent to final chamber 58 and about twenty degrees (20°) counterclockwise from the tangent line. As will be discussed in further detail below, slots 57 direct the partially mixed first and second components from within intermediate chamber 56 into final chamber 58. Although shown as a pair of opposed openings, it is envisioned that spray tip assembly 50 may include only a single slot 57 (FIG. 6A), or may alternatively include three or more slots 57 (shown in phantom, FIG. 6A). Outlet 59 is configured to atomize the thoroughly mixed solution into a cone-shaped spray. As shown, from proximal to distal, outlet 59 includes a first cylindrical portion 59*a*, a second cylindrical portion 59*b*, and a recessed portion 59*c*. It is envisioned, however, that outlet 59 may be formed without second cylindrical portion 59*b*.

The operation of applicator assembly 10 will now be described as relates to the figures. Prior to use, insert 40 is received within intermediate chamber 56 of spray tip assembly 50. As discussed above, insert 40 is positioned such that fluid passing through intermediate chamber 56 is forced around insert 40 in the space created by ribs 56*a*. Spray tip assembly 50 is selectively received on distal end 30*b* of elongated shaft 30. As discussed above, manifold 20 may be integrally formed with elongated shaft 30, or instead it may be necessary to secure elongated shaft 30 to manifold 20 manually prior to use, making sure that first and second component channels 23, 25 are aligned with first and second component lumen 33, 35. First and second source of component (not shown) are next connected to first and second proximal extensions 22, 24, respectively. Once secured to manifold 20, first and second source of components may be activated, e.g. depression of syringe plungers (not shown), to initiate the flow of first and second components within first and second component channels 23, 25, respectively. The first and second components flow through first and second component channels 23, 25, through first and second component lumen 33, 35, respectively, and into spray tip assembly 50.

The first and second components flowing from first and second component lumen 33, 35 encounter insert 40 retained with intermediate chamber 56. First and second component lumen 33, 35 are spaced such that the first and second components may flow around insert 40 in the space created by ribs 56a in between insert 40 and spray tip assembly 50. The initially mixed first and second components are then forced into slots 57 where they are directed radially inward toward final chamber 58. The flow of the mixture through slots 57 imparts a swirling motion to the mixture as the mixture enters final chamber 58. Thereafter, the thoroughly mixed solution is atomized as it is ejected through outlet 59 in a cone-shaped spray.

Figure 7:
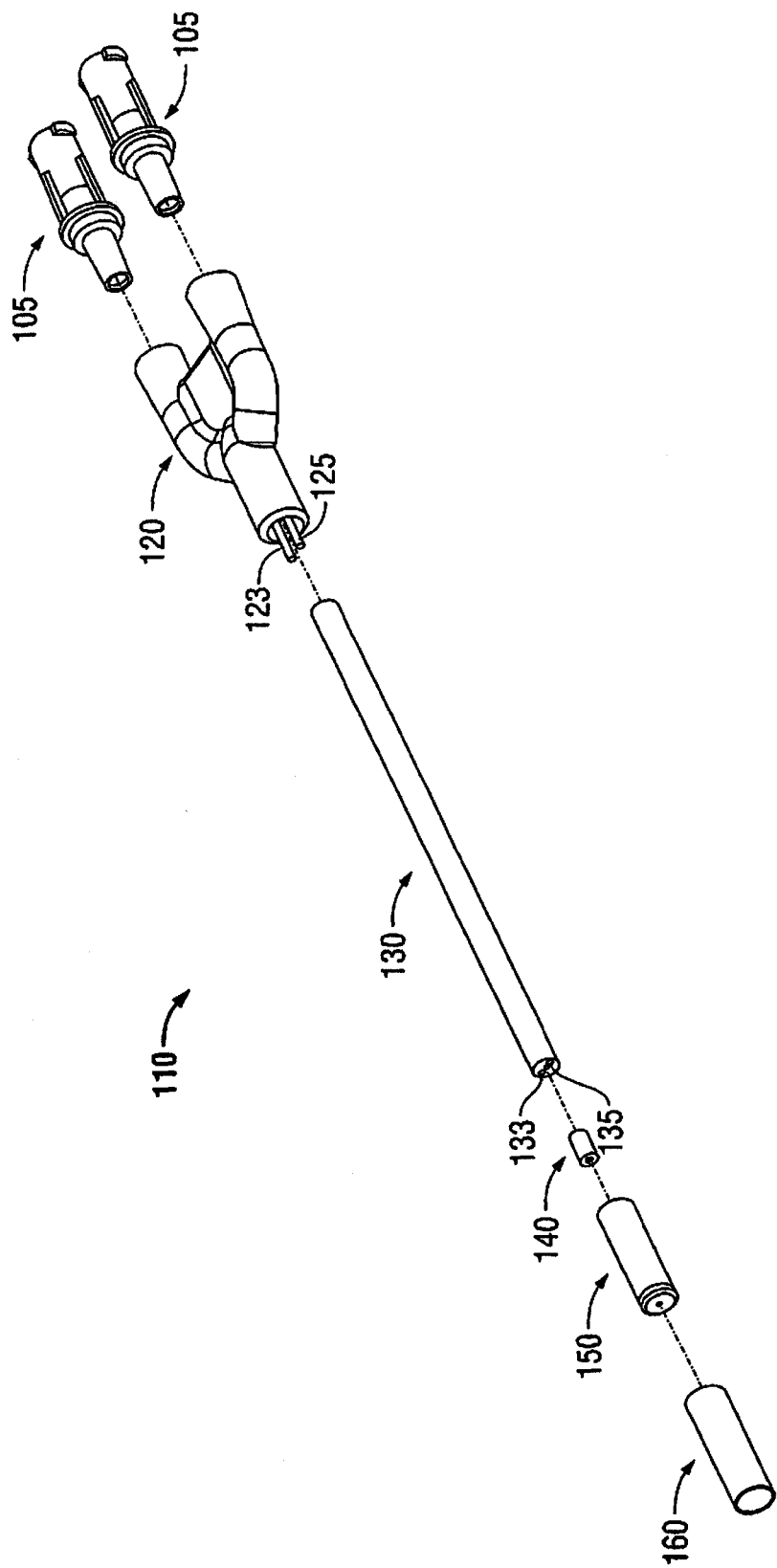
FIG. 7 is an exploded perspective view of an applicator assembly according to another embodiment of the present disclosure.

Turning to FIGS. 7-10, an alternate embodiment of the present disclosure is shown generally as applicator assembly 110. Applicator assembly 110 is substantially similar to applicator assembly 10, and will therefore only be described as relates to the differences therebetween. With reference initially to FIGS. 7 and 8, applicator assembly 110 includes a manifold or base 120 configured to receive a pair of check valves 105, an elongated shaft 130 extending from manifold 120, and a spray tip assembly 150 positioned on a distal end of elongated shaft 130. An insert 140 is received within spray tip assembly 150 and a shrink tube 160 is received about spray tip assembly 150.

Referring to FIG. 7, first and second component channels 123, 125 extend from a distal end of manifold 120. First and second component channels 123, 125 are configured to fluidly communicate with first and second component lumen 133, 135 extending through elongated shaft 130. This configuration permits for a more secure fluid seal between manifold 120 and elongated shaft 130.

Figure 10:
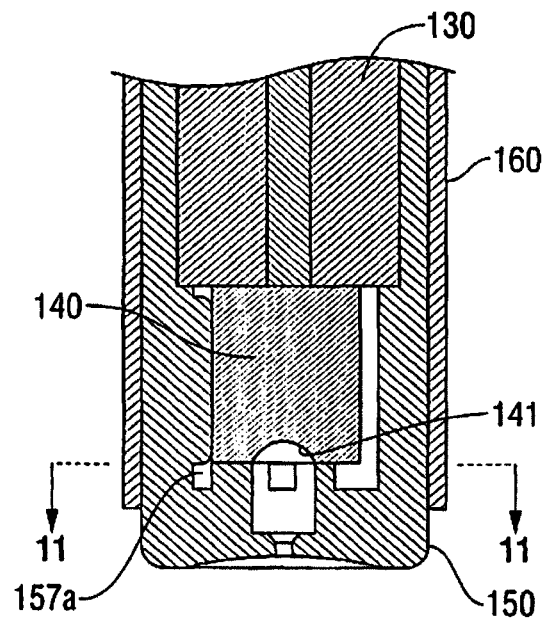
FIG. 10 is an enlarged cross-sectional view of section 10 of FIG. 9.

With reference now to FIGS. 9 and 10, insert 140 is substantially similar to insert 40, including a substantially cylindrical member configured to be received within spray tip assembly 150. As shown, insert 140 includes hemispherical recess 141 on both a first and second end thereof, however, it is envisioned that hemispherical recess 141 may be formed on a single end thereof. Recess 141 is configured to create turbulence in the flow of the first and second components as they encounter insert 140, thereby assisting in the mixing of the components.

Still referring to FIGS. 9 and 10, shrink tube 160 is received about spray tip assembly 150 to prevent the excess radial expansion/flexion of spray tip assembly 150 during operation. Shrink tube 160 may also assist in securing spray tip assembly 150 to elongated shaft 130.

Figure 11:
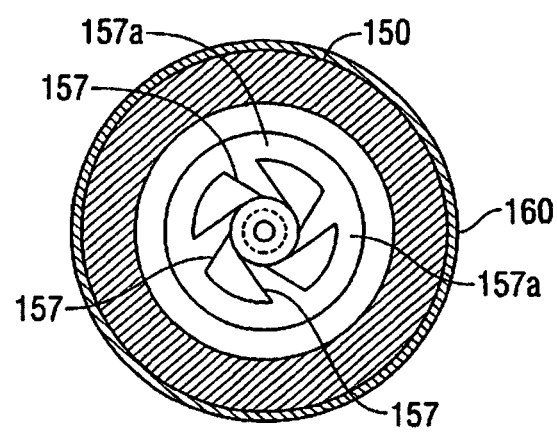
FIG. 11 is a cross-sectional view of the spray tip assembly of FIG. 9 taken along line 11-11 of FIG. 10.

With reference now to FIG. 11, spray tip assembly 150 is substantially similar to spray tip assembly 50, described hereinabove, including radially extending slots 157. A gutter or annular recess 157a is formed about slots 157. Gutter 157a is configured to direct the partially mixed first and second components into slots 157.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

The invention claimed is:

1. An applicator assembly for dispensing a mixture, the assembly comprising:
    a first portion defining first and second component lumens each having proximal and distal ends, the proximal ends of the first and second component lumens being configured for fluid communication with respective first and second sources of component;
    a second portion defining a mixing chamber, the distal end of the first and second component lumens being in fluid communication with the mixing chamber;
    a third portion defining an outlet in fluid communication with the mixing chamber; and
    an insert disposed within the mixing chamber between the first and second component lumens and the outlet, the insert and the third portion operating to define at least one channel and an annular recess formed about the at least one channel for directing partially mixed first and second components towards the outlet.

2. The applicator assembly of claim 1, further including a first source of component and a second source of component.

3. The applicator assembly of claim 2, wherein the first and second sources of components are syringes.

4. The applicator assembly of claim 1, wherein the outlet defines a substantially circular cross-section.

5. The applicator assembly of claim 1, wherein the outlet is configured to atomize the mixed first and second components.

6. The applicator assembly of claim 1, wherein the first portion includes a substantially Y-shaped manifold.

7. The applicator assembly of claim 1, wherein the second portion includes a substantially circular cross-section.

8. The applicator assembly of claim 1, wherein the third portion includes a substantially circular cross-section.

9. The applicator assembly of claim 1, wherein the second portion and the insert are configured to mix the first and second components as the components pass through the mixing chamber.

10. The applicator assembly of claim 1, wherein the second portion and the insert are configured to mix the first and second components prior to the components passing through the outlet.

11. The applicator assembly of claim 1, wherein the second portion includes ribs for maintaining the insert in a spaced relationship from an inner wall.

12. The applicator assembly of claim 1, wherein the insert includes a recess formed in at least a first end thereof.

13. The applicator assembly of claim 12, wherein the recess is substantially hemispherical.

14. An applicator assembly for dispensing a mixture, the assembly comprising:
    a first portion defining first and second component lumens each having proximal and distal ends, the proximal ends of the first and second component lumens being configured for fluid communication with respective first and second sources of component;
    a second portion defining a mixing chamber, the distal end of the first and second component lumens being in fluid communication with the mixing chamber;
    a third portion defining an outlet in fluid communication with the mixing chamber; and
    an insert disposed within the mixing chamber between the first and second component lumens and the outlet, the insert including a cylindrical member having a recess formed in a first end thereof.

15. The applicator assembly of claim 14, wherein an outer diameter of the insert is uniform along an entire length of the insert.

16. The applicator assembly of claim 14, wherein the recess formed in the first end of the insert is substantially hemispherical.

17. The applicator assembly of claim 14, further including a shrink tube about at least the second and third portions.

* * * * *